(12) United States Patent
Smith et al.

(10) Patent No.: US 6,361,963 B1
(45) Date of Patent: Mar. 26, 2002

(54) BIOFILM GROWTH DEVICE

(75) Inventors: Kelly S. Smith; Mike Mayer, both of Jacksonville; Claudia deSouza, Atlantic Beach; Fred L. Singleton, Switzerland, all of FL (US)

(73) Assignee: Hercules Incorporated, Wilmington, DE (US)

( * ) Notice: Subject to any disclaimer, the term of this patent is extended or adjusted under 35 U.S.C. 154(b) by 0 days.

(21) Appl. No.: 09/631,146

(22) Filed: Aug. 2, 2000

(51) Int. Cl.[7] .................................................. C12Q 1/02
(52) U.S. Cl. ....................... 435/29; 435/30; 435/287.1; 73/53.03; 73/53.06
(58) Field of Search ........................... 435/287.1, 4, 29, 435/30; 73/53.01, 53.03, 53.06, 61.41, 61.59, 61.52, 64.41, 64.56

(56) References Cited

U.S. PATENT DOCUMENTS

| | | | |
|---|---|---|---|
| 1,813,991 A | 7/1931 | Eaton | |
| 2,090,077 A | 8/1937 | Thorne | |
| 2,320,577 A | 6/1943 | Dunn | |
| 2,660,884 A | * 12/1953 | Dean | |
| 3,332,745 A | 7/1967 | Bailey et al. | |
| 3,503,250 A | 3/1970 | Cotton et al. | |
| 3,718,030 A | 2/1973 | Kesler | |
| 3,943,754 A | 3/1976 | Orr, Jr. | |
| 4,090,850 A | 5/1978 | Chen et al. | |
| 4,753,775 A | 6/1988 | Ebersole et al. | |
| 4,889,692 A | 12/1989 | Hotzman | |
| 4,908,319 A | 3/1990 | Smyczek et al. | |
| 5,049,492 A | 9/1991 | Sauer et al. | 435/30 |
| 5,051,359 A | 9/1991 | Characklis | 435/32 |
| 5,096,676 A | 3/1992 | McPherson et al. | 422/245 |
| 5,369,011 A | 11/1994 | Ebersol et al. | 435/7.32 |
| 5,462,874 A | 10/1995 | Wolf et al. | 435/297.5 |
| 5,536,363 A | 7/1996 | Nguyen | 162/5 |
| 5,618,429 A | 4/1997 | Moller-Bremer | 210/610 |
| 5,624,815 A | 4/1997 | Grant et al. | 435/30 |
| 5,641,458 A | 6/1997 | Shockley, Jr. et al. | 422/102 |
| 5,792,430 A | 8/1998 | Hamper | 422/131 |
| 5,858,791 A | 1/1999 | Lemaire | 436/25 |
| 5,958,762 A | * 9/1999 | Stoppini et al. | 435/297.5 |
| 6,017,459 A | * 1/2000 | Zeiher et al. | 210/650 |
| 6,053,032 A | 4/2000 | Kraus et al. | 73/61.62 |

* cited by examiner

Primary Examiner—David A. Redding
(74) Attorney, Agent, or Firm—Hoffmann & Baron, LLP

(57) ABSTRACT

A method and apparatus for determining the effect of various agents on the growth of biological material (biofilm), microbially-influenced corrosion and the deposition of organic and inorganic contaminants is disclosed. The method and apparatus allow for the modeling of the growth of biological contaminants and the deposition of organic and inorganic materials on industrial equipment surfaces, such as those used in the pulp and papermaking industry. The device consists of a tray which includes recessed areas for receiving coupons, as well as fluid inlets and fluid outlets for permitting the flow of liquid samples over the coupons. The design and configuration of the apparatus provides a great deal of versatility in testing various biocidal and other agents under select environmental conditions.

37 Claims, 4 Drawing Sheets

BIOFILM GROWTH DEVICE

FIELD OF THE INVENTION

The present invention relates to a method and apparatus for studying and screening agents useful for regulating the growth of biological material and the deposition of organic and inorganic contaminants on coupons. More particularly, the present invention is directed to a method and apparatus for studying and screening biocidal agents useful in regulating the growth of bacteria on stainless steel coupons.

BACKGROUND OF RELATED TECHNOLOGY

Many industrial processes, such as pulp and paper making, utilize water and/or other liquid material in processing steps. Such process liquid typically provides an excellent supply of carbon and nutrients which promote bacterial growth. In paper mills, for instance, bacterial films ("biofilms") undesirably and readily form on the steel surfaces of process equipment used during manufacture. Such biofilms typically are accompanied by protective exopolysaccharides ("slime") and occur at the interface of these equipment surfaces and process water streams. Additionally, inorganic contaminants, such as calcium carbonate ("scale") and organic contaminants often deposit on such surfaces. These organic contaminants are typically known as pitch (e.g., resins from wood) and stickies (e.g., glues, adhesives, tape, and wax particles).

The growth of biofilm and the deposition of these inorganic and organic contaminants can be detrimental to the efficiency of such equipment causing both reduced product quality, reduced operating efficiency, and general operational difficulties in the systems. Biofilm growth and organic and inorganic contaminant deposition on consistency regulators and other instrument probes can render these components useless, and such growth and deposition on screens can reduce throughput and upset operation of the system. Growth and deposition can occur not only on metal surfaces in the system, but also on plastic and synthetic surfaces such as machine wires, felts, foils, Uhle boxes and headbox components. The difficulties posed by these growths and deposits include direct interference with the efficiency of the contaminated surface, resulting in reduced production, as well as holes, dirt, and other sheet defects that reduce the quality and usefulness of the paper for operations that follow like coating, converting or printing.

Consequently, methods of preventing and removing the build-up of such growths and deposits on pulp and paper mill equipment surfaces are of great industrial importance. While paper machines can be shut down for cleaning, this is undesirable as it necessarily results in a loss of productivity and the product which results prior to such cleaning is of poor quality as it is partially contaminated from growths and deposits which break off and become incorporated into product sheets. Likewise, removing growths and deposits also necessarily results in the formation of poor quality product which is manufactured prior to such removal. Preventing biofilm growth and contaminant deposition is thus greatly preferred as it allows for consistently high quality product to be produced in an efficient manner. Particularly, the use of compositions comprising gelatin, such as those described in U.S. Pat. No. 5,536,363 to Nguyen, have been found to be well suited for regulating the deposition of organic and inorganic contaminants in pulp and papermaking systems.

The growth of slime on metal surfaces creates an environment which is conducive to corrosion. This microbially-influenced corrosion typically occurs at the interface between the slime and the metal surface. Also, fouling or plugging by slime readily occurs in pulp and paper mill systems. Typically, the slime becomes entrained in the paper produced and causes breakouts on the paper machines with consequent work stoppages and the loss of production time. It also causes unsightly blemishes in the final product, resulting in rejects and wasted output. These contamination problems have resulted in the extensive utilization of biocides in water used in pulp and paper mill systems. Agents which have enjoyed widespread use in such applications include chlorine, organo-mercurials, chlorinated phenols, organo-bromines, and various organo-sulfur compounds, all of which are generally useful as biocides but each of which is attended by a variety of impediments.

Known means of studying biological material typically involve the flow of an aqueous sample containing the biological material over a solid support, such as with a flow through cell assembly. Typically, a pressure means, such as an inert gas, and/or a vacuum means are used to cause the sample to contact the solid support. For example, U.S. Pat. No. 5,641,458 to Shockley, Jr. et al. discloses a flow through cell device for the non-invasive monitoring of bodily fluids. The device includes sensors which interact with a fluid sample through a semi-permeable membrane. Sensors attached to the membrane allow for photochemical reactions involving the fluid sample to be monitored optically.

U.S. Pat. No. 5,624,815 to Grant et al. discloses a method and apparatus for analyzing biological material by passing a liquid sample through a number of discrete wells which are adapted to retain the biological material. The liquid sample is drawn into the wells through a vacuum mechanism. Also, U.S. Pat. No. 5,792,430 to Hamper, U.S. Pat. No. 5,624,815 to Grant et al., U.S. Pat. No. 4,908,319 to Smyczek et al., and U.S. Pat. No. 4,753,775 to Ebersole et al., all disclose means for studying biological material in which a liquid sample is drawn over a solid support.

As conditions such as temperature, pH, and the presence of organic and inorganic materials can vary greatly among and within manufacturing processes, there is a continuing need to investigate materials useful for the prevention and removal of biofilms and organic and inorganic contaminants that form on process equipment functioning under these various conditions. Known experimental techniques, such as those described above, are not well suited for such investigations. While they are suited for the specific investigation of certain biological material, they do not allow for an efficient and thorough analysis of the effect of numerous and various chemicals and compositions on a variety of substrates under select conditions.

Additionally, it is known to monitor biofilm growth in water systems, such as through the apparatuses and methods described in U.S. Pat. No. 5,049,492 to Sauer et al. and U.S. Pat. No. 6,017,459 to Zeiher et al., to allow for the sampling of water during manufacturing processes. While these apparatuses and methods are important in determining, and consequently maintaining, the quality of the water stream, of greater importance is the discovery and development of compositions which will prevent and/or destroy the growth of biofilms and inorganic and organic contaminants in the water stream. Therefore, there exists a need for a model experimental system and a method involving such a system by which the efficient investigation of substances useful in regulating the growth of biological materials and the deposition of inorganic and organic contaminants on equipment surfaces such as those used in pulp and papermaking processes may be conducted.

SUMMARY OF THE INVENTION

In one aspect, the present invention provides a device for permitting fluid flow, such as whitewater or synthetic whitewater endemic to pulp and papermaking systems, over a coupon. The device includes a tray body (tray) which defines a coupon receiving chamber, a fluid inlet passageway in fluid communication with the coupon receiving chamber, and a fluid outlet passageway in fluid communication with the coupon receiving chamber. The tray body provides for fluid to enter the fluid inlet passageway, contact the coupon, and enter the fluid outlet passageway.

Preferably, the tray body is a substantially elongate member including first and second opposed side surfaces, first and second opposed major surfaces, with the coupon receiving chamber accessible through the first major surface. The tray body may include a plurality of coupon receiving chambers which are adapted to receive substantially elongate stainless steel coupons.

The coupon receiving chamber is in partial overlying registry with the fluid inlet passageway and the fluid outlet passageway and includes a coupon support surface and an upstanding perimetrical wall bounding the coupon support surface. The coupon support surface further defines a fluid inlet port in fluid communication with the fluid inlet passageway and further defines a fluid outlet port in fluid communication with the fluid outlet passageway. The tray body further defines a fluid inlet aperture which is opposite the fluid inlet port and which is in fluid communication with the fluid inlet passageway.

The tray body accommodates a fluid feed conduit for delivering a fluid through the fluid inlet aperture and further defines a fluid outlet aperture which is opposite the fluid outlet port and which is in fluid communication with the fluid outlet passageway. Further, the tray body accommodates a fluid discharge conduit for conducting fluid through the fluid outlet aperture.

In a preferred embodiment of the present invention, the coupon support surface is elongate and the fluid inlet and fluid outlet ports are defined at opposite ends of the coupon support surface. The present invention may also include a cover which is in removable sealing registry over the coupon receiving chamber. Additionally, the present invention may also include a gasket supported between the tray body and the cover for further sealing the coupon receiving chamber.

In a method aspect of the present invention, a method is provided for studying and screening agents useful for regulating the growth of biofilm and the deposition of organic and inorganic contaminants on a coupon surface which includes the steps of: (i) providing a device which regulates fluid flow over the coupon surface, wherein the device includes a tray body defining a coupon receiving chamber, a fluid inlet passageway in fluid communication with the coupon receiving chamber and a fluid outlet passageway in fluid communication with the coupon receiving chamber; (ii) placing the coupon in the coupon receiving chamber; and (iii) effecting a fluid flow over the coupon. The present invention may also include the step of determining the growth of biological material on the coupon, such as by subjecting the coupon to staining and microscopy.

The present invention may further include the step of directing the fluid flow through the fluid inlet passageway and directing the fluid flow to the fluid inlet passageway by a fluid feed conduit. Further, the present invention may include the step of directing the fluid flow across the coupon, through the fluid outlet passageway, and from the fluid outlet passageway through a fluid discharge conduit.

DETAILED DESCRIPTION OF THE INVENTION

Figure 1:
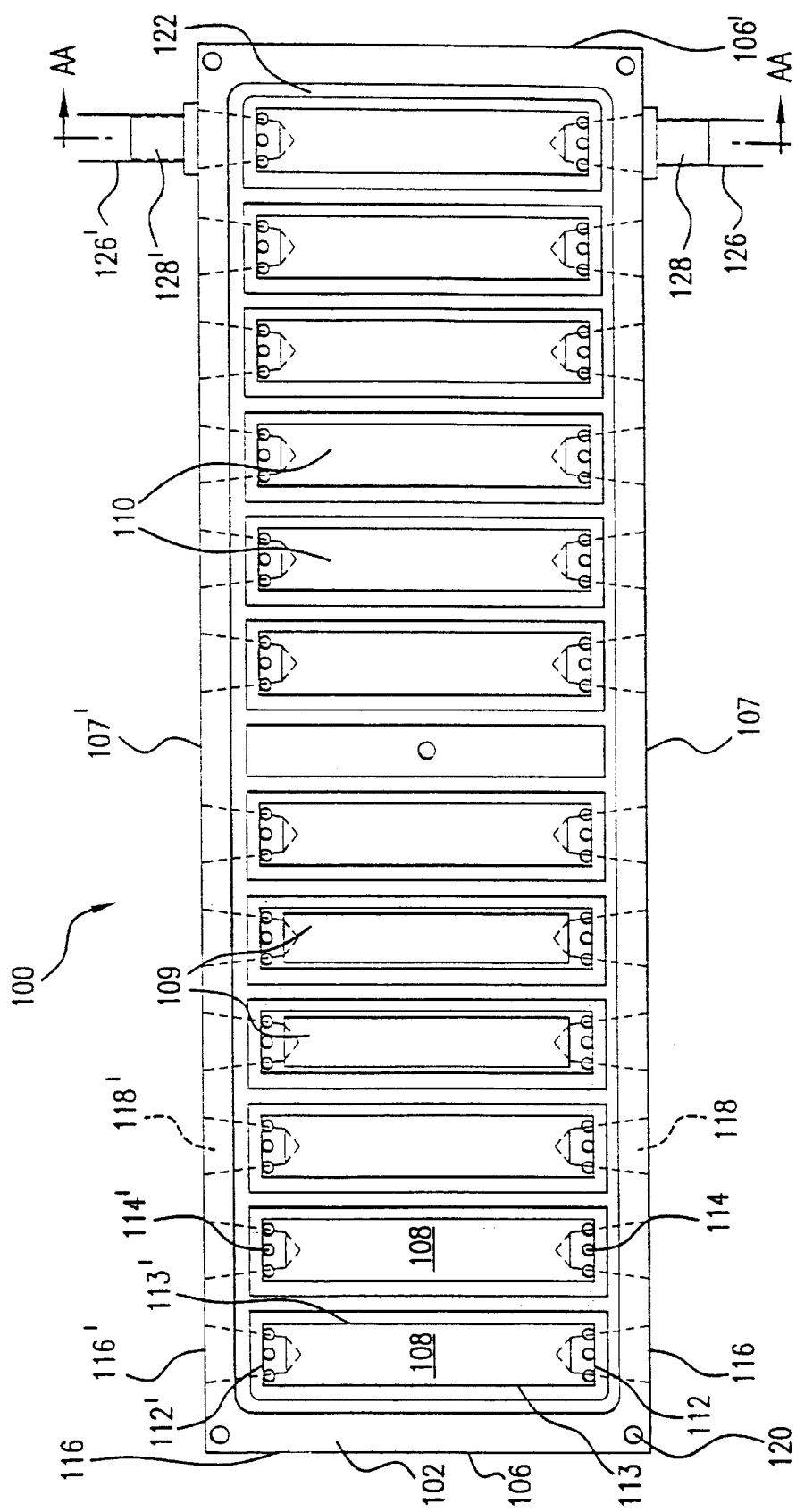
FIG. 1 is a top plan view of a biofilm growth tray of the present invention.

The present invention is well suited for studying the growth of biological materials and the deposition of organic and inorganic contaminants on various substrates. Such biological materials include, for example, bacteria, fungi, yeast, algae, diatoms, protozoa, macroalgae, and the like. In the pulp and paper industry, process water provides an excellent supply of organic and inorganic materials which promote the growth of bacteria (biofilms) and protective exopolysaccharides (slime) which occur at the interface of machine surfaces (typically steel) and process water streams. Additionally, inorganic contaminants, such as calcium carbonate ("scale") and organic contaminants often deposit on such surfaces. These organic contaminants are typically known as pitch (e.g., resins from wood) and stickies (e.g., glues, adhesives, tape, and wax particles). The present invention allows for compositions to be studied or screened which will serve to destroy or prevent the growth of such biofilms and slime and the deposition of such organic and inorganic contaminants. The present invention further may be used to monitor corrosion on such surfaces as well as the efficacy of corrosion-preventing agents.

Turning to FIGS. 1–4, a biofilm growth device of the present invention is shown. The device consists of a tray 100 defining one or more chambers 108 which are of an appropriate size to accommodate a material being investigated. Such material under investigation is typically referred to in the art as a coupon 109 and is of such composition, size, and shape as to model the surfaces of equipment used in industrial processes. Tray 100 is an elongate generally rectangular member having opposing first and second major planar surfaces 102 and 104, opposing transverse side surfaces 106 and 106', and opposing longitudinal side surfaces 107 and 107'. It will be recognized by one of skill in the art that the tray 100 may be manufactured of any suitable material such as plastic or metal and may be of any suitable shape and size. Desirably, the tray 100 is made of steel, in order to model equipment surfaces used in pulp and papermaking processes.

Each chamber 108 of tray 100 includes a recessed coupon support surface 110 for receiving a coupon 109 being investigated. Each chamber 108 is generally rectangular, is open at the top, and includes a perimetrical wall bounding the coupon support surface 110. The perimetrical wall is defined by opposing transverse side surfaces 112 and 112' and opposing longitudinal side surfaces 113 and 113'. Each chamber 108 further includes at least one fluid inlet port 114 and at least one fluid outlet port 114' at each end thereof. Desirably, fluid inlet port 114 and fluid outlet port 114' are defined by the coupon support surface 110 of each chamber 108. It will be recognized by one of skill in the art that these chambers 108 can be of any suitable size and shape for purposes of the present invention.

As shown in FIGS. 1–4, chambers 108 are of such length to accommodate coupons 109 commonly used in research investigations. Further, it is desired that a plurality of chambers 108 of uniform shape and size be utilized in the present invention and that such chambers 108 are spaced apart from one another in a uniform manner. In such an arrangement, the present invention can be efficiently manufactured and easily adapted to simulate a variety of environmental conditions. Further, such an arrangement allows for a variety of biocidal and other agents to be screened simultaneously.

It is contemplated that the present invention may also be a tray defining a single chamber of any shape and size or may define multiple chambers of various shapes and sizes which are different than those shown in FIGS. 1–4. Such arrangements are contemplated as may be necessary to meet the unique demands of a particular screening procedure.

Figure 2:
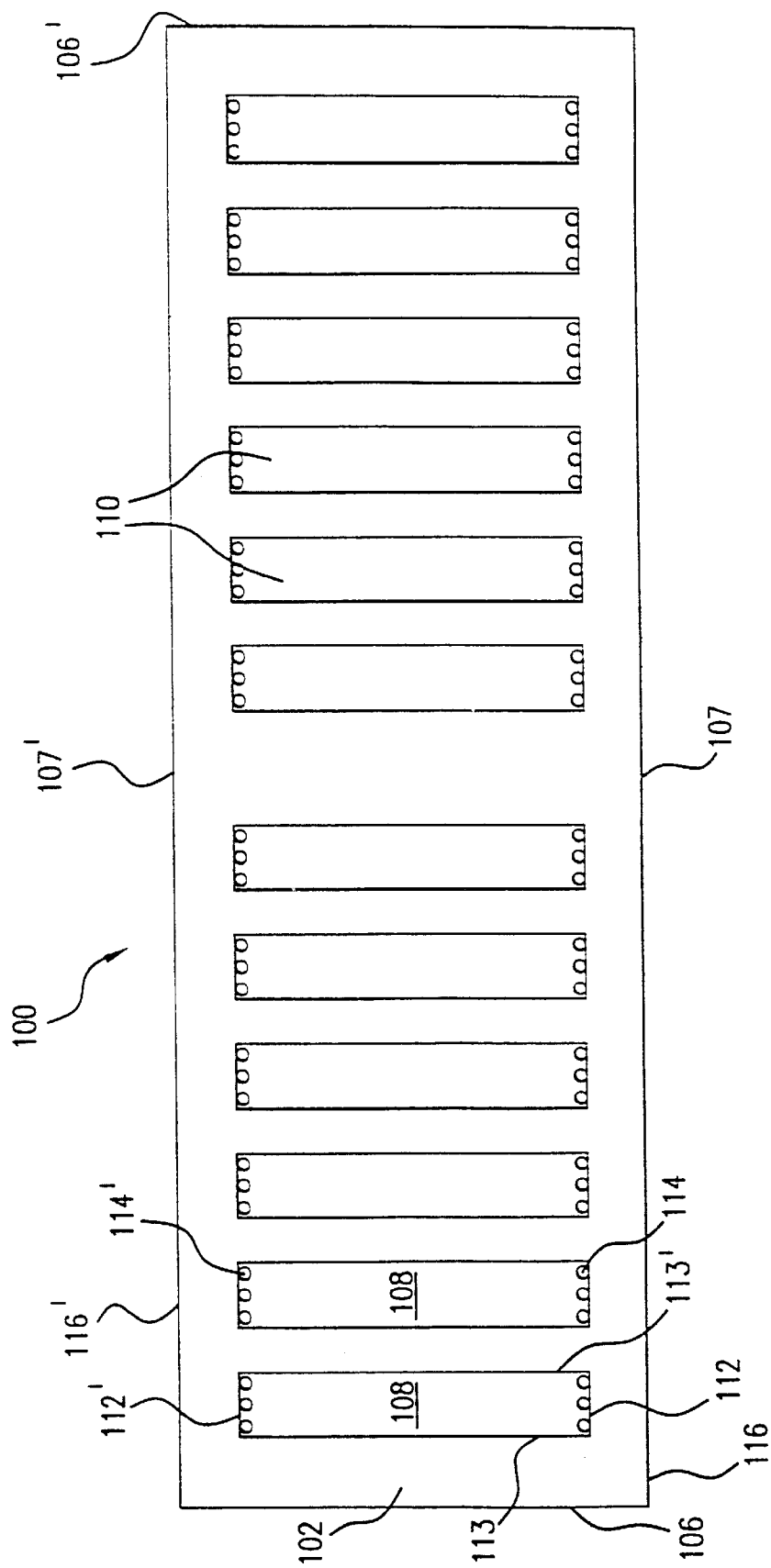
FIG. 2 is a top view of the present invention showing a tray defining a plurality of chambers and fluid inlet and fluid outlet ports.
Figure 3:
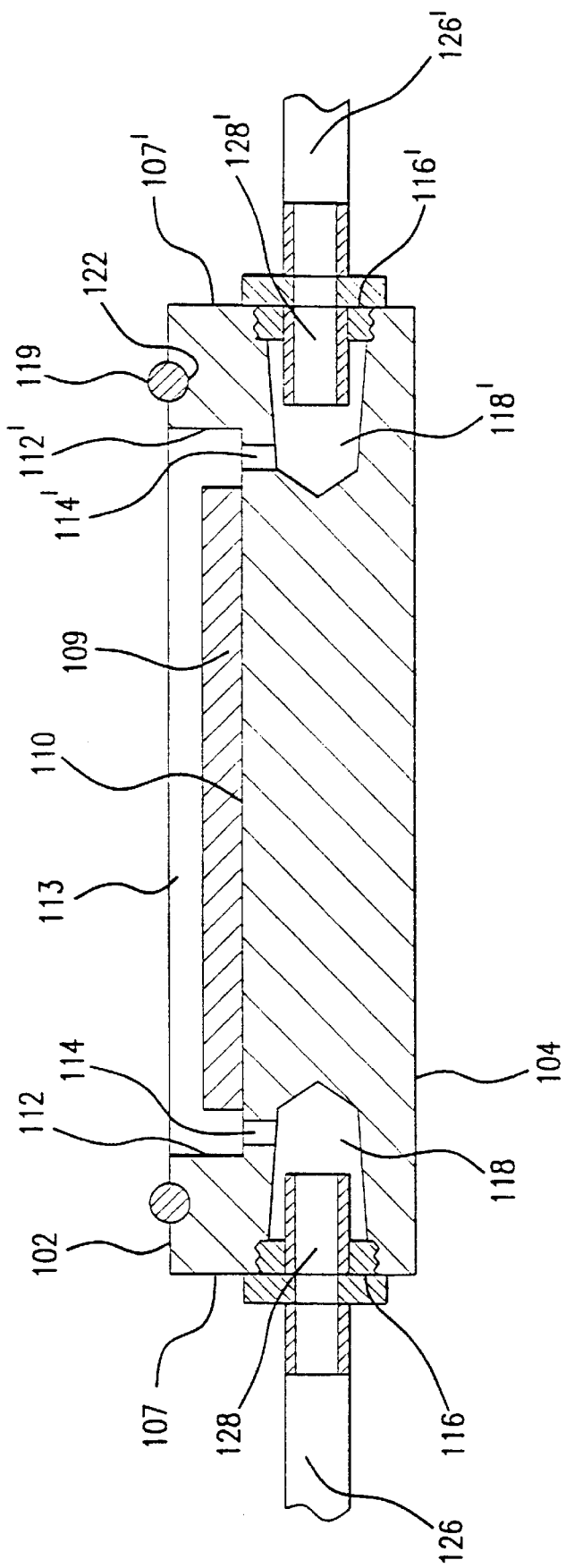
FIG. 3 is a cross-sectional view of the tray of FIG. 1 taken along the line AA—AA.
Figure 4:
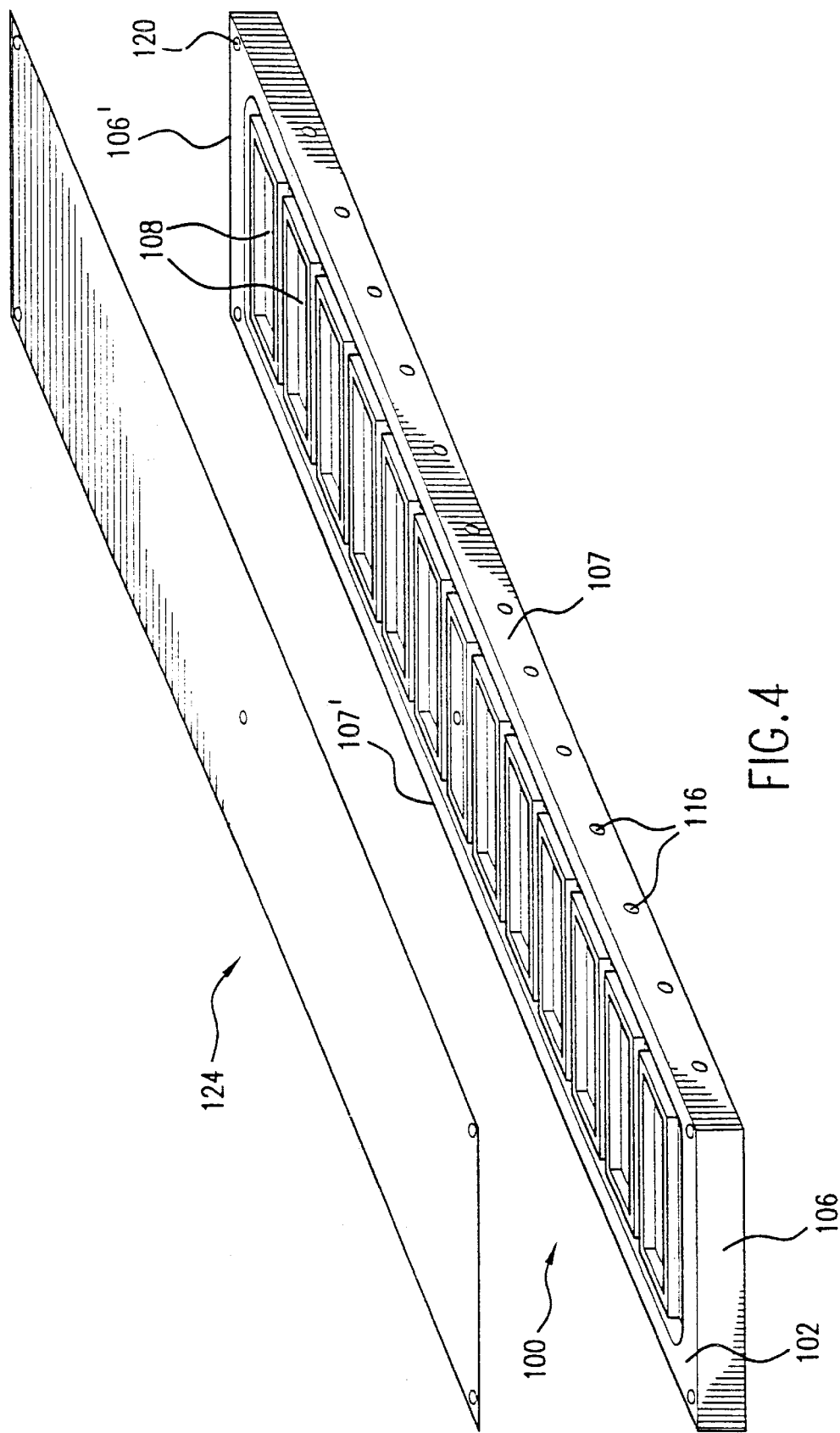
FIG. 4 is an exploded perspective view of the tray of the present invention including a cover thereover.

Turning again to FIGS. 1–4, fluid inlet ports 114 and fluid outlet ports 114' are spaced apart such that the coupon 109 being investigated will rest therebetween. The fluid inlet port 114 and fluid outlet port 114' are of such number, shape and size as to permit a desired flow of liquid over the surface of the coupon 109 being investigated. For example, as shown in FIGS. 1, 2, and 4, it has been found that when three fluid inlet ports 114 and three fluid outlet ports 114' are used and are circular in shape, a desired flow of sample liquid, such as that which occurs during pulp and papermaking processes, is realized over the surface of the coupon 109 being investigated. As such, the present invention is capable of modeling the flow of liquid over equipment surfaces in a variety of industrial processes. As will be recognized by one of skill in the art, fluid inlet ports 114 and fluid outlet ports 114' can exist in any number of configurations as necessary to achieve a desired flow of liquid over the coupon 109 being investigated and as to allow for the efficient manufacture thereof.

Each chamber 108 also has associated therewith at least on fluid inlet aperture 116 for supplying liquid samples to a chamber 108 and a fluid outlet aperture 116' for removing the liquid sample after it has passed over the coupon 109 being investigated. As illustrated in FIG. 3, these apertures 116 and 116' are in fluid communication with the coupon support surface 110 of each chamber 108. Such fluid communication is defined by fluid inlet and fluid outlet passageways 118 and 118', respectively, and fluid inlet and fluid outlet ports 114 and 114', respectively. As will be recognized by one of skill in the art, fluid inlet aperture 116 and fluid outlet aperture 116' may be present in many configurations.

In one desired aspect of the present invention, fluid inlet and fluid outlet apertures 116 and 116', respectively, are bored into opposing longitudinal side surfaces 107 and 107', respectively, of tray 100 and are adapted for receiving a fluid feed conduit 126 and a fluid discharge conduit 126', respectively, as shown in FIGS. 1 and 3. For example, these apertures 116 and 116' are desirably tapped for helical thread to provide a mating connector for receiving pipe thread. As shown in FIGS. 1 and 3, fluid inlet and fluid outlet nozzles 128 and 128' are threaded into fluid inlet and fluid outlet apertures 116 and 116', respectively. Fluid feed and fluid discharge conduits 126 and 126', which may be rubber tubing, are attached to fluid inlet and fluid outlet nozzles 128 and 128', respectively. Further, fluid inlet and fluid outlet passageways 118 and 118', respectively, are bored into tray 100 through opposing side surfaces 106 and 106', respectively, as shown in FIGS. 1 and 3.

Tray 100 is desirably adapted for receiving a cover 124, as shown in FIG. 4, which may be secured to tray 100 with screws at screw receiving recesses 120. Cover 124 is of such size and shape to substantially enclose the open upper end of tray 100. A rubber gasket 119, shown in FIG. 3, may be provided between tray 100 when cover 124 is secured thereto by inserting such gasketing 119 into a recessed area 122 of tray 100. Recessed area 122 is defined by first major surface 102 of tray 100 so as to receive the rubber gasketing 119 which has elongate holes therein which correspond to the size, shape, and position of chambers 108, such that the coupon support surfaces 110 of chambers 108 are not covered by the gasketing 119. As such, when a cover 124 manufactured of non-opaque material, such as clear plastic, is utilized, a researcher can observe the fluid flow over a coupon 109 seated in the coupon support surfaces 110 of chambers 108. It will be recognized by one of skill in the art that the use of a cover 124 and/or gasketing 119 is not required in the present invention, but both are desirable as their combined use permits the efficient control of ambient conditions to which a coupon 109 being investigated is exposed.

As stated above, the present invention is suitable for use in investigating the growth of biofilm and the deposition of organic and inorganic contaminants on a coupon 109. The present invention is further suitable for use in monitoring microbially-influenced corrosion of coupon 109 which results from such contamination as well as the efficacy of corrosion-preventing agents. This coupon 109 may be of any suitable material, such as metal or plastic, and may be of any suitable size and shape. Desirably, the coupon 109 will be of such size and shape to fit into the recessed coupon support surface 110 of chamber 108 such that a flow of water entering chamber 108 from fluid inlet port 114 will flow across the surface of the coupon 109 in a desired manner, such as at a rate which simulates the rate of flow over industrial machine surfaces. Examples of such coupons are described in U.S. Pat. No. 4,142,402 to Mattioli, et al. For example, in the paper and pulp industry, biofilm growth typically occurs on stainless steel machine parts. Consequently, stainless steel coupons would desirably be used to model the surfaces of such machines in order to investigate materials that may be useful for the prevention and/or destruction of such biofilm growth.

Additionally, the test conditions of the twelve chambers can be arranged in any grouping; for example, to test three different slime control agents plus a negative control with no agent added, four groups of three chambers can be used. Each group desirably draws bacteria and growth medium from a single reservoir. The design of the tray provides a great deal of versatility in experimental design. For example, slime control agents can be tested both for prevention of biofilm growth and for removal of established biofilms, simply by changing the time at which the agents are added to the fluid during the experiment.

EXAMPLE

In one desired aspect of the present invention, a stainless steel tray 100 defines twelve chambers 108, as shown in FIGS. 1, 2 and 4. Tray 100, a clear plastic cover 124, a gasket 119, twelve stainless steel coupons 109 (approximately two and one half inches by one half inch), twenty four pieces of flexible rubber tubing, five pairs of forceps, and four carboy stopper assemblies were cleaned, autoclaved and allowed to dry overnight in a drying oven. The cleanings were done in a manner known in the art. For instance, the coupons 109 were cleaned with warm water and detergent and placed in a ten percent solution of bleach overnight. They were then rinsed with distilled water, cleaned with detergent, placed in a one percent acetone solution and sonicated for thirty minutes.

In accordance with the agents being investigated, various protocols were used as indicated below:

Pure Culture/Defined Mixtures of Laboratory Bacteria

Four nine-liter carboys that accept the stopper assemblies above were filled with two liters of a salts medium. Stir bars were then added to each carboy which were capped with foil, and the carboys were autoclaved. The carboys were removed from the autoclave such that the liquid cooled to room temperature prior to use. Two small flask cultures (25 ml each) were inoculated with the bacterial species tested and were incubated overnight.

The cultures of bacteria were then spun down at 3500 rpm for twenty minutes at 20° C. and resuspended in the salt mixture in each carboy to a final optical density of approximately 0.024. A copy of the spectrophotometer readings was then obtained.

Synthetic White Water Experimentation

Synthetic White Water was formulated as shown in Table 1:

this whitewater was added 1 g/L of yeast extract, as for example Difco brand yeast extract and Fisher Scientific brand yeast extract, which was allowed to mix overnight and covered with autoclaved aluminum foil.

For experimentation involving each of the above samples, once the above preparations were made, peristaltic pumps were assembled such that for all twelve chambers 108, twelve pump heads sized for quarter-inch tubing, four motors, and four controllers were used. For each chamber 108, quarter-inch tubing was attached to a fluid outlet nozzle 128' associated with fluid outlet aperture 116' on one end thereof and to a pump head on the other end thereof. The tray 100 was assembled by placing coupons 109 in each chamber 108 that was being investigated. Where machine surfaces involved in pulp and papermaking processes were under investigation, stainless steel coupons 109 were used. The cover 124 was then secured to tray 100 with five screws at screw receiving recesses 120 to form a tight seal between the tray 100, cover 124, and gasket member 119 which was positioned within a recessed area 122 of tray 100.

The carboy and stoppers were then assembled. In experiments in which recirculated flow was desired, the tray fluid discharge conduit 126' was then attached to the stoppers. The tray fluid feed conduit 126 was then attached to the stoppers, but not to the tray 100. The stoppers were lifted

TABLE 1

| Enriched Synthetic White Water Concentrate Composition | | | |
|---|---|---|---|
| Component | mg/L*dH$_2$O (1X) | mg/L dH$_2$O (2X) | Alternate formulation in mg/L |
| CaCl$_2$ | 111 | 222 | CaCl$_2$.2(H$_2$O) 147(1X), 294(2X) |
| MgSO$_4$ | 60 | 120 | |
| NaHCO$_3$ | 168 | 336 | |
| K$_2$HPO$_4$ | 140 | 280 | |
| NH$_4$Cl | 480 | 960 | |
| FeCl$_3$.6(H$_2$O) | 1.04 | 2.08 | FeCl$_3$ anhyd. 0.62(1X), 1.24(2X) |
| Na$_2$EDTA | 1.48 | 2.96 | Na$_2$EDTA.2(H$_2$O) 3.28(2X) |
| Dextrose | 3000 | 6000 | Starch 10(1X), 20(2X) |
| Yeast extract[1] | 1000 | 2000 | |
| HEPES[2] (pH 7) | 0.05 | 0.10 | |
| MES[3] (pH 5.5) | 9.76 | 19.52 | |
| Tricine (pH 8) | 8.96 | 17.92 | |

*All components are measured in mg/L expect HEPES, which is measured in M/L
[1]For example, Difco brand yeast extract, or Fisher Scientific brand yeast extract
[2]HEPES is 4-(2-hydroxyethyl)-1-piperazine ethanesulfonic acid
[3]MES is beta-morpholinoethansulfonaseure hydrate The pH of the final composition was adjusted using either NaOH or HCl.

For experimentation using synthetic whitewater, the carboys were autoclaved empty (except for stir bars) and allowed to cool to room temperature. Eight liters of distilled water were autoclaved in large Erlenmeyer flasks capped with foil and allowed to cool overnight. Two large graduated cylinders, capped with foil, were also autoclaved and allowed to cool overnight. 100 ml of the 2×synthetic whitewater concentrate was then added to each carboy. This was then diluted with 1900 ml of sterile deionized water, measured using the autoclaved graduated cylinders.

Whitewater Experimentation

For experimentation using whitewater, the carboys were autoclaved empty (except for stir bars) and were allowed to cool to room temperature. The sterile carboys were filled with two liters of whitewater, as measured with a sterile graduated cylinder. The carboys were arranged next to the tray 100 and placed on stir plates where they were mixed. To and the above samples under investigation were added to the carboys. Additionally, 1 or 2 ml of the sample was collected and stored in a sterile container for plating and optical density readings. The stoppers were then fixed in place by wrapping Parafilm® around the stopper and the neck of the carboy.

The pumps were then primed by taking a sterile 5 or 10 ml pipette attached to a battery-powered pipettor and inserting them into the fluid feed conduit 126 that was not yet connected to the fluid inlet aperture 116. The pipettor was then run so that fluid was drawn up through the fluid feed conduit 126 until it began to fill the pipette, at which time the tubing was clamped off two to three inches from the end and attached to a fluid inlet nozzlel 128 threaded into fluid inlet aperture 116. This procedure was repeated for all fluid feed conduits 126.

For each group of three chambers 108 whose pumps were on one controller, the clamps were removed from the fluid feed conduits 126. The pumps were immediately started and maintained at approximately the same speed. Each chamber 108 in which a coupon 109 was being investigated was then monitored to ensure that the liquid sample flowed over each coupon 109 in a desired manner, and did not fill the chamber. Desirably, a thin layer of fluid covered the coupons 109. Chambers 108 that filled up with liquid sample were drained.

After a designated period of time, each motor was shut off and the fluid feed conduit 126 was again clamped. The cover 124 was then removed from the tray 100. The coupons 109 were removed and replaced with clean, sterile coupons for the next experiment, with both removal and replacement occurring through the use of sterile forceps. The used coupons 109 were set aside for analysis, including staining and microscopy.

The example set forth above serves to illustrate the present invention, but in no way is intended to limit the spirit and scope thereof, which is defined by the following claims.

What is claimed is:

1. A device for permitting fluid flow over a coupon, comprising:
    a tray body defining a coupon receiving chamber, said tray body further defining a fluid inlet passageway in fluid communication with said coupon receiving chamber, and a fluid outlet passageway in fluid communication with said coupon receiving chamber, whereby said tray body provides for fluid to enter said fluid inlet passageway, contact said coupon, and enter said fluid outlet passageway, wherein said tray further defines a fluid inlet aperture in fluid communication with said fluid inlet passageway and opposite said fluid inlet port.

2. The device of claim 1, wherein said tray is a substantially elongate member including first and second opposed longitudinal side surfaces and first and second opposed planar surfaces, said coupon receiving chamber accessible through said first planar surface and defining an open upper end of said coupon receiving chamber.

3. The device of claim 1, wherein said coupon receiving chamber is in partial overlying registry with said fluid inlet passageway and said fluid outlet passageway.

4. The device of claim 1, where said coupon receiving chamber includes a coupon support surface and an upstanding perimetrical wall bounding said coupon support surface.

5. The device of claim 1 wherein said fluid inlet passageway, said fluid outlet passageway, and said coupon receiving chamber permit the flow of a fluid selected from the group consisting of whitewater and synthetic whitewater, wherein said whitewater and said synthetic whitewater are endemic to pulp and papermaking systems.

6. The device of claim 4, wherein said coupon support surface further defines a fluid inlet port in fluid communication with said fluid inlet passageway.

7. The device of claim 4, wherein said coupon support surface further defines a fluid outlet port in fluid communication with said fluid outlet passageway.

8. The device of claim 4, wherein said coupon support surface is elongate and wherein said fluid inlet and fluid outlet ports are defined at opposite ends thereof.

9. The device of claim 1, wherein said tray accommodates a fluid feed conduit for delivering a fluid through said fluid inlet aperture.

10. The device of claim 1, wherein said tray further defines a fluid outlet aperture in fluid communication with said fluid outlet passageway opposite said fluid outlet port.

11. The device of claim 10, wherein said tray accommodates a fluid discharge conduit for conducting fluid through said fluid outlet aperture.

12. The device of claim 1, further comprising a cover in removable sealing registry over said coupon receiving chamber.

13. The device of claim 12, further comprising a gasket supported between said tray and said cover for further sealing said coupon receiving chamber.

14. The device of claim 12, further comprising a plurality of said coupon receiving chambers.

15. The device of claim 1, further comprising a coupon.

16. The device of claim 15, wherein said coupon is formed from stainless steel.

17. The device of claim 15, wherein said coupon is substantially elongate.

18. A device for subjecting a coupon to a fluid flow, comprising:
    a substantially elongate tray body defining a coupon receiving chamber, a fluid inlet passageway in fluid communication with said coupon receiving chamber, and a fluid outlet passageway in fluid communication with said coupon receiving chamber;
    wherein said coupon receiving chamber includes a coupon support surface and an upstanding perimetrical wall bounding said coupon support surface and wherein said coupon support surface defines a fluid inlet port in fluid communication with said fluid inlet passageway and a fluid outlet port in fluid communication with said fluid outlet passageway; and
    wherein said tray further defines a fluid inlet aperture in fluid communication with said fluid inlet passageway opposite said fluid inlet port and a fluid outlet aperture in fluid communication with said fluid outlet passageway opposite said fluid outlet port, whereby said tray body provides for fluid to enter said fluid inlet passageway, contact said coupon, and enter said fluid outlet passageway.

19. The device of claim 18, wherein said tray accommodates a fluid feed conduit in fluid communication with said fluid inlet aperture.

20. The device of claim 18, wherein said tray accommodates a fluid discharge conduit in fluid communication with said fluid outlet aperture.

21. The device of claim 18, wherein said coupon support surface is elongate and wherein said fluid inlet and fluid outlet ports are defined at opposite ends thereof.

22. The device of claim 18, further comprising a cover in removable sealing registry over said coupon receiving chamber.

23. The device of claim 22, further comprising a gasket supported between said tray and said cover for further sealing said coupon receiving chamber.

24. The device of claim 18, wherein said fluid inlet passageway, said fluid outlet passageway, and said coupon receiving chamber permit the flow of a fluid selected from the group consisting of whitewater and synthetic whitewater, wherein said whitewater and said synthetic whitewater are endemic to pulp and papermaking systems.

25. The device of claim 18, further comprising a plurality of said coupon receiving chambers.

26. The device of claim 18, further comprising a coupon.

27. The device of claim 26, wherein said coupon is formed from stainless steel.

28. A method for determining agents useful for studying the growth of biofilm and the deposition of organic and inorganic materials on a coupon surface, comprising the steps of:
    providing a device which regulates fluid flow over said coupon surface, said device comprising a tray body defining a coupon receiving chamber, a fluid inlet passageway in fluid communication with said coupon receiving chamber and a fluid outlet passageway in fluid communication with said coupon receiving chamber;

placing said coupon in said coupon receiving chamber; and effecting a fluid flow over said coupon.

29. A method of claim 28, wherein said agents are useful for regulating the growth of biofilm and the deposition of organic and inorganic materials on said coupon surface.

30. A method of claim 28, wherein said agents are useful for regulating corrosion of said coupon surface.

31. A method of claim 28, further comprising the step of determining the growth of biological material on said coupon.

32. A method of claim 31, wherein said determining step is effected by subjecting said coupon to staining and microscopy.

33. A method of claim 28, further comprising the step of determining the deposition of organic and inorganic materials on said coupon.

34. A method of claim 28, wherein said effecting step further comprises directing said fluid flow through said fluid inlet passageway.

35. A method of claim 34, wherein said effecting step further comprises directing said fluid flow to said fluid inlet passageway by a fluid feed conduit.

36. A method of claim 28, wherein said effecting step further comprises directing said fluid flow across said coupon and through said fluid outlet passageway.

37. A method of claim 28, wherein said effecting step further comprises directing said fluid flow from said fluid outlet passageway and through a fluid discharge conduit.

* * * * *

UNITED STATES PATENT AND TRADEMARK OFFICE
CERTIFICATE OF CORRECTION

PATENT NO. : 6,361,963 B1
DATED : March 26, 2002
INVENTOR(S) : Smith et al.

It is certified that error appears in the above-identified patent and that said Letters Patent is hereby corrected as shown below:

Column 8,
Line 61, the printed patent incorrectly reads "nozzlel" should read -- nozzle --.

Signed and Sealed this

Twenty-fifth Day of June, 2002

Attest:

Attesting Officer

JAMES E. ROGAN
Director of the United States Patent and Trademark Office